US007128759B2

(12) United States Patent
Osborne et al.

(10) Patent No.: US 7,128,759 B2
(45) Date of Patent: Oct. 31, 2006

(54) IMPLANTABLE MEDICAL DEVICE WITH CONSTRAINED EXPANSION

(75) Inventors: Thomas A. Osborne, Bloomington, IN (US); Brian C. Case, Bloomington, IN (US); Jacob A. Flagle, Bloomington, IN (US); Andrew K. Hoffa, Bloomington, IN (US); Michael L. Garrison, Indianapolis, IN (US)

(73) Assignee: Cook Incorporated, Bloomington, IN (US)

( * ) Notice: Subject to any disclaimer, the term of this patent is extended or adjusted under 35 U.S.C. 154(b) by 120 days.

(21) Appl. No.: 10/849,639

(22) Filed: May 19, 2004

(65) Prior Publication Data
US 2004/0243222 A1    Dec. 2, 2004

Related U.S. Application Data

(60) Provisional application No. 60/471,647, filed on May 19, 2003.

(51) Int. Cl.
*A61F 2/06* (2006.01)
(52) U.S. Cl. ..................................... 623/1.24
(58) Field of Classification Search ............ 623/1.1, 623/1.11–1.14, 1.24–1.29, 1.36
See application file for complete search history.

(56) References Cited

U.S. PATENT DOCUMENTS 4,580,568 A    4/1986    Gianturco
5,855,601 A    1/1999    Bessler et al.
6,231,598 B1   5/2001    Berry et al.
6,299,635 B1   10/2001   Frantzen
6,371,983 B1   4/2002    Lane
6,464,720 B1   10/2002   Boatman et al.
6,494,909 B1   12/2002   Greenhalgh
6,508,833 B1   1/2003    Pavcnik et al.
2001/0039450 A1   11/2001   Pavcnik et al.
2002/0177894 A1   11/2002   Acosta et al.
2003/0181974 A1   9/2003    Xie et al.

FOREIGN PATENT DOCUMENTS

WO    WO 01/54625 A1    8/2002

*Primary Examiner*—Corrine McDermott
*Assistant Examiner*—Wiliam H Matthews
(74) *Attorney, Agent, or Firm*—Dunlap, Codding & Rogers, P.C.

(57) ABSTRACT

Medical devices for implantation in a body vessel are provided. A medical device according to the invention comprises a support structure and one or more graft members comprising a valve portion and a constraining portion. The support structure has a first, unexpanded configuration and a second, expanded configuration. The constraining portion is adapted to substantially prevent the support structure from achieving the second, expanded configuration. The valve portion is adapted to permit fluid flow through a body vessel in a first direction and substantially prevent fluid flow through the vessel in a second, opposite direction.

15 Claims, 6 Drawing Sheets

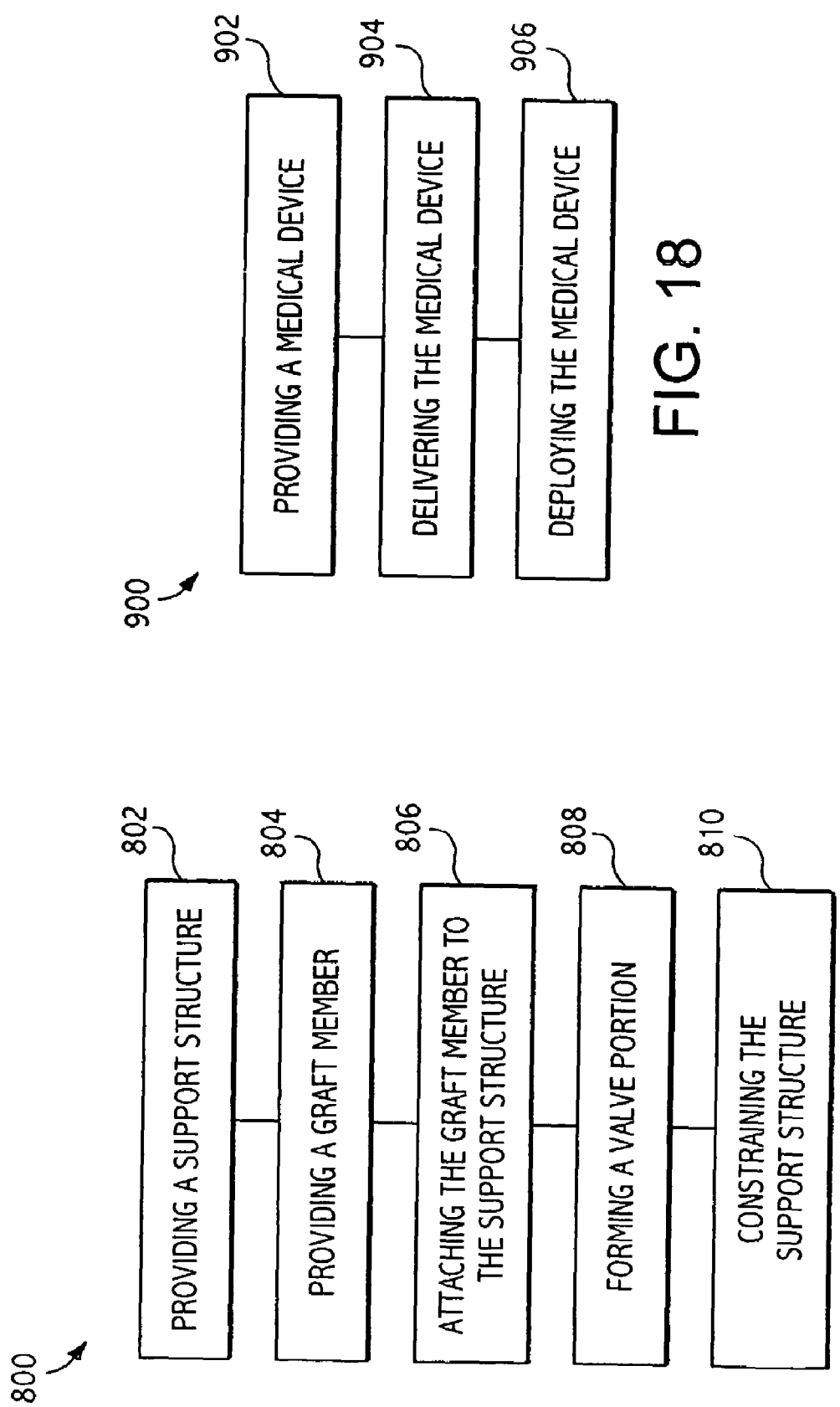

IMPLANTABLE MEDICAL DEVICE WITH CONSTRAINED EXPANSION

CROSS-REFERENCE TO RELATED APPLICATION

This application claims priority to U.S. Provisional Application Ser. No. 60/471,647, filed on May 19, 2003, the entire disclosure of which is hereby incorporated into this disclosure in its entirety.

FIELD OF THE INVENTION

The present invention relates to medical devices. More particularly, the invention relates to medical devices for implantation in a body vessel.

BACKGROUND OF THE INVENTION

Many vessels in animals transport fluids from one bodily location to another. Frequently, fluid flows in a unidirectional manner along the length of the vessel. Varying fluid pressures over time, however, can introduce a reverse flow direction in the vessel. In some vessels, such as mammalian veins, natural valves are positioned along the length of the vessel and act as one-way check valves that open to permit the flow of fluid in the desired direction, and quickly close upon a change in pressure, such as a transition from systole to diastole, to prevent fluid flow in a reverse direction, i.e., retrograde flow.

While natural valves may function for an extended time, some may lose effectiveness, which can lead to physical manifestations and pathology. For example, venous valves are susceptible to becoming insufficient due to one or more of a variety of factors. Over time, the vessel wall may stretch, affecting the ability of the valve leaflets to close. Furthermore, the leaflets may become damaged, such as by formation of thrombus and scar tissue, which may also affect the ability of the valve leaflets to close. Once valves are damaged, venous valve insufficiency may be present, and can lead to discomfort and possibly ulcers in the legs and ankles.

Current treatments for venous valve insufficiency include the use of compression stockings that are placed around the leg of a patient in an effort to force the vessel walls radially inward to restore valve function. Surgical techniques are also employed in which valves can be bypassed or replaced with autologous sections of veins with competent valves.

Minimally invasive techniques and instruments for placement of intraluminal medical devices have developed over recent years. A wide variety of treatment devices that utilize minimally invasive technology has been developed and includes stents, stent grafts, occlusion devices, infusion catheters and the like. Minimally invasive intravascular devices have especially become popular with the introduction of coronary stents to the U.S. market in the early 1990's. Coronary and peripheral stents have been proven to provide a superior means of maintaining vessel patency, and have become widely accepted in the medical community. Furthermore, the use of stents has been extended to treat aneurisms and to provide occlusion devices, among other uses.

Recently, prosthetic valves have been developed that use a support structure such as a stent. Frequently, a graft member is attached to the support structure and provides a valve function to the device. For example, the graft member can be in the form of a leaflet that is attached to a stent and movable between first and second positions. In a first position, the valve is open and allows fluid flow to proceed through a vessel in a first direction, and in a second position the valve is closed to prevent fluid flow in a second, opposite direction. An example of this type of prosthetic valve is described in commonly owned U.S. Pat. No. 6,508,833, to Pavcnik for a MULTIPLE-SIDED INTRALUMINAL MEDICAL DEVICE, which is hereby incorporated by reference in its entirety. In other examples of prosthetic valves, a tube that terminates in leaflets is attached to one or more support structures to form a valve. The leaflets open to permit fluid flow in a first direction in response to fluid pressure on one side of the leaflets, and close to prevent fluid flow in a second, opposite direction in response to fluid pressure on opposite sides of the leaflets. An example of this configuration is provided in U.S. Pat. No. 6,494,909 to Greenhalgh for AN ENDOVASCULAR VALVE, which is hereby incorporated by reference in its entirety.

Support structures in some medical devices, such as stent grafts, can exert an outwardly-directed radial force upon an interior wall of a body vessel in which such a medical device is implanted. The exertion of such a force has potential to induce an inflammatory response or other effect within the body vessel and/or the surrounding tissue. Accordingly, medical devices with constrained expansion are desirable.

SUMMARY OF EXEMPLARY EMBODIMENTS OF THE INVENTION

The invention provides medical devices for implantation in a body vessel.

In one exemplary embodiment, a medical device according to the invention comprises a support structure having a first, unexpanded configuration and a second, expanded configuration, and a graft member connected to the support structure. The a graft member comprises a valve portion and a constraining portion. The valve portion is adapted to permit fluid flow through a body vessel in a first direction and substantially prevent fluid flow through the vessel in a second, opposite direction. The constraining portion is adapted to substantially prevent the support structure from achieving the second, expanded configuration.

In one exemplary embodiment, a medical device according to the invention comprises a support structure and first and second graft members connected to the support structure. Each of the graft members comprises a valve portion and a constraining portion. The valve portions are disposed substantially opposite one another and are adapted to permit fluid flow through a body vessel in a first direction and substantially prevent fluid flow through the vessel in a second, opposite direction. The constraining portions cooperate to substantially prevent the support structure from achieving the second, expanded configuration.

In one exemplary embodiment, a medical device according to the invention comprises a support structure having a first, unexpanded configuration and a second, expanded configuration, means for preventing the support structure from achieving the second, expanded configuration, and means for regulating fluid flow through a body vessel.

In one exemplary embodiment, a medical device according to the invention comprises a support structure having a first, unexpanded configuration and a second, expanded configuration, a first valve leaflet connected to the support structure and comprising a first valve portion and a first constraining portion, and a second valve leaflet connected to the support structure and comprising a second valve portion and a second constraining portion. The first and second valve portions cooperatively regulate fluid flow through a body vessel, and the first and second constraining portions cooperatively prevent the support structure from achieving the second, expanded configuration.

In one exemplary embodiment, a medical device according to the invention comprises a support structure having a first, unexpanded configuration and a second, expanded configuration. The device further comprises a first graft member attached to the support structure, having a first edge, and adapted to permit fluid flow through said vessel in a first direction and substantially prevent fluid flow through said vessel in a second, opposite direction. The device further comprises a second graft member attached to the support structure, having a second edge, and adapted to substantially prevent the support structure from achieving the second, expanded configuration. The first and second edges cooperatively define an opening adapted to permit a controlled amount of fluid flow through a body vessel in the second, opposite direction.

The invention also provides methods of making a medical device. In one exemplary embodiment, a method of making according to the invention comprises providing a support structure having a first, unexpanded configuration and a second, expanded configuration, providing a graft member, attaching the graft member to the support structure, forming a valve portion in the graft member, and constraining the support structure to substantially prevent the support structure from achieving the second, expanded configuration.

The invention also provides methods of treating a patient. In one exemplary embodiment, a method of treating a patient according to the invention comprises providing a medical device comprising a support structure having a first, unexpanded configuration and constrained from achieving a second, expanded configuration, and a graft member attached to the support structure, the graft member comprising a valve portion adapted to permit fluid flow through said vessel in a first direction and substantially prevent fluid flow through said vessel in a second, opposite direction. The method of treating further comprises delivering the medical device to a point of treatment in a body vessel, and deploying the medical device at the point of treatment.

The invention includes other embodiments within the scope of the claims, and variations of all embodiments, and is limited only by the claims made by the applicant. Additional understanding of the invention can be obtained by referencing the detailed description of exemplary embodiments of the invention, below, and the appended drawings.

BRIEF DESCRIPTION OF THE DRAWINGS

FIG. 17 is a flow chart of a method of making a medical device according to the invention.

FIG. 18 is a flow chart of a method of treatment according to the invention.

DETAILED DESCRIPTION OF EXEMPLARY EMBODIMENTS OF THE INVENTION

Figure 1:
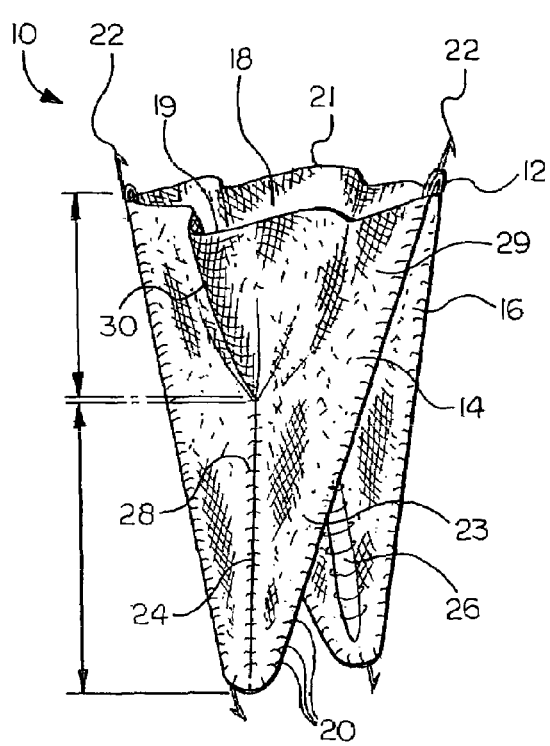
FIG. 1 is a perspective view of a medical device according to a first exemplary embodiment of the invention.
Figure 2:
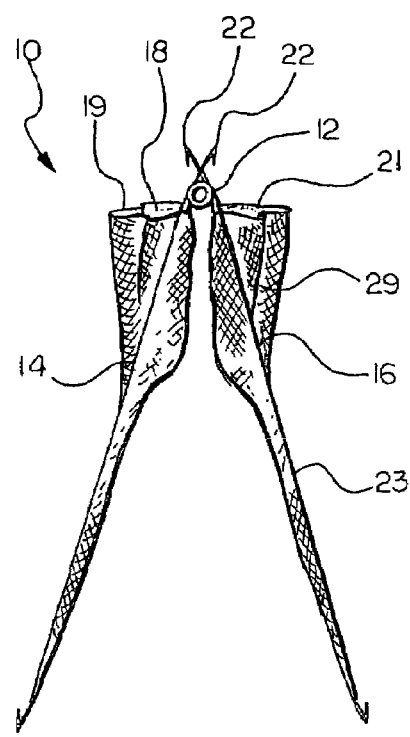
FIG. 2 is a side view of the medical device illustrated in FIG. 1.

The following detailed description and appended drawings describe and illustrate various exemplary embodiments of the invention. The description and drawings serve to enable one skilled in the art to make and use the invention, and are not intended to limit the scope of the invention or its protection in any manner.

The invention provides medical devices for implantation in a body vessel, methods of making the medical devices, and methods of treatment that utilize the medical devices.

FIGS. 1 through 6 illustrate a medical device 10 according to a first exemplary embodiment of the invention. The device 10 is an implantable medical device that comprises a support structure 12 and first 14 and second 16 graft members attached to the support structure 12.

As used herein, the term "implantable" refers to an ability of a medical device to be positioned at a location within a body, such as within a body vessel. Furthermore, the terms "implantation" and "implanted" refer to the positioning of a medical device at a location within a body, such as within a body vessel.

A wide variety of support structures are known in the art, and any suitable support structure can be utilized. The support structure chosen need only provide a structure for attachment of the graft members 14, 16. A support structure that provides a stenting function, i.e., exerts a radially outward force on the interior of the vessel in which the device 10 is implanted, can be utilized if desired. By including a support structure that provides a stenting function, the medical device 10 can provide both stenting and valving functionality at a point of treatment.

The stent art provides numerous examples of support structures acceptable for use in the medical device 10, and any suitable stent support structure can be used. The specific support structure chosen will depend on several factors, including the vessel in which the medical device is being implanted, the axial length of the treatment site, the number of valves desired in the device, the inner diameter of the vessel, the delivery method for placing the support structure, and others. Those skilled in the art can determine an appropriate support structure based on these and other factors.

The support structure 12 is an expandable support structure having a first, unexpanded configuration and a second, expanded configuration. The support structure 12 can be either balloon- or self-expandable. Also, the support structure can be formed from a variety of materials, and need only be biocompatible, or able to be made biocompatible, and provide for the attachment of the graft members 14, 16 and stenting function, if desired. Examples of suitable materials include, without limitation, stainless steel, nickel titanium (NiTi) alloys, e.g., Nitinol, other shape memory and/or superelastic materials, polymers, and composite materials. A resorbable material can also be used for the support structure 12. As used herein, the term "resorbable" refers to the ability of a material to be absorbed into a tissue and/or body fluid upon contact with the tissue and/or body fluid. A number of resorbable materials are known in the art, and any suitable resorbable material can be used. Examples of suitable types of resorbable materials include resorbable homopolymers, copolymers, or blends of resorbable polymers. Specific examples of suitable resorbable materials include poly-alpha hydroxy acids such as polylactic acid, polylactide, polyglycolic acid (PGA), or polyglycolide; trimethlyene carbonate; polycaprolactone; poly-beta hydroxy acids such as polyhydroxybutyrate or polyhydroxyvalerate; or other polymers such as polyphosphazines, polyorganophosphazines, polyanhydrides, polyesteramides, polyorthoesters, polyethylene oxide, polyester-ethers (e.g., polydioxanone) or polyamino acids (e.g., poly-L-glutamic acid or poly-L-lysine). There are also a number of naturally derived resorbable polymers that may be suitable, including modified polysaccharides, such as cellulose, chitin, and dextran, and modified proteins, such as fibrin and casein.

Suitable support structures can also have a variety of configurations, including braided strands, helically wound strands, ring members, consecutively attached ring members, tube members, and frames cut from solid tubes. Also, suitable support structures can have a variety of sizes. The exact configuration and size chosen will depend on several factors, including the desired delivery technique, the nature of the vessel in which the device will be implanted, and the size of the vessel. The support structure can be sized so that the second, expanded configuration is larger in diameter that the inner diameter of the vessel in which the device will be implanted. This sizing can facilitate maintenance of the device in the vessel following implantation.

Examples of suitable support structures for use in the medical devices of the invention include those described in U.S. Pat. No. 6,508,833 to Pavcnik et al. for a MULTIPLE-SIDED INTRALUMIINA MEDICAL DEVICE; U.S. Pat. No. 6,464,720 to Boatman et al. for a RADIALLY EXPANDABLE STENT; U.S. Pat. No. 6,231,598 to Berry et al. for a RADIALLY EXPANDABLE STENT; U.S. Pat. No. 6,299,635 to Frantzen for a RADIALLY EXPANDABLE NON-AXIALLY CONTRACTING SURGICAL STENT; U.S. Pat. No. 4,580,568 to Gianturco for a PERCUTANEOUS ENDOVASCULAR STENT AND METHOD FOR INSERTION THEREOF; and published application for United States Patent 2,001,0039450 to Pavcnik et al. for an IMPLANTABLE MEDICAL DEVICE, all of which are hereby incorporated by reference in their entirety.

The support structure 12 can include structural features, such as barbs 22, that maintain the support structure 12 in position following implantation in a body vessel. The art provides a wide variety of structural features that are acceptable for use in the medical device 10, and any suitable structural feature can be used. Furthermore, barbs 22 can also comprise separate members attached to the support structure 12 by suitable attachment means and techniques, such as welding and bonding.

A wide variety of materials acceptable for use as the graft members 14, 16 are known in the art, and any suitable material can be utilized. The material chosen need only be able to perform as described herein, and be biocompatible, or able to be made biocompatible. Examples of suitable materials include flexible materials, natural materials, synthetic materials, and combinations thereof. Examples of suitable natural materials include collagen, extracellular matrix (ECM) materials, such as submucosa, and other bioremodellable materials, such as bovine pericardium. Small intestine submucosa (SIS) is particularly well-suited for use as the graft members 14, 16. Other examples of ECM materials that can be used for the graft member include stomach submucosa, liver basement membrane, urinary bladder submucosa, tissue mucosa, and dura mater. ECMs are particularly well suited materials for use in the graft member, at least because of their abilities to remodel and become incorporated into adjacent tissues. These materials can provide a scaffold onto which cellular in-growth can occur, eventually allowing the material to remodel into a structure of host cells.

Examples of suitable synthetic materials include polymeric materials, such as polypropylene, polyurethane, and expanded polytetrafluoroethylene (ePTFE).

As best illustrated in FIGS. 1 through 4, free edges 19, 21 of the graft members 14, 16 cooperatively define an opening 18. The graft members 14, 16 can be attached to the support structure 12 with any suitable attachment mechanism, such as sutures 20, adhesives, bonding, and the like. The attachment mechanism chosen will depend on the nature of the support structure 12 and graft members 14, 16. Sutures 20 provide an acceptable attachment mechanism when SIS or other ECM materials are used as the graft members 14, 16 with a metal or plastic support structure.

The device 10 can include any suitable number of graft members. The graft members need only be able to provide the functionality described herein. The specific number chosen will depend on several factors, including the type and configuration of the support structure 12. As illustrated in FIGS. 1 through 6, two graft members 14, 16 are suitable for use in devices 10 comprising a support structure configured in accordance with this embodiment, but a single graft member, or three or more graft members, can also be used.

The graft members 14, 16 comprise a constraining portion 23 and a valve portion 29. The constraining portion is adapted to substantially prevent the support structure 12 from achieving the second, expanded configuration. This prevents the valve portion 29 from becoming completely taught. The constraining portion 23 is sized such that, as the support structure expands from the first configuration to the second configuration, the constraining portion 23 becomes taught, substantially preventing further expansion of the support structure 12. As described more fully below, the constraining portion 23 can be sized such that the constrained configuration of the device 10 is slightly larger in diameter than the inner diameter of the vessel in which the device will be implanted, but less than a vessel inner diameter at which an adverse effect may occur, such as vessel rupture. This sizing can facilitate maintenance of the device 10 in the vessel following implantation.

Figure 3:
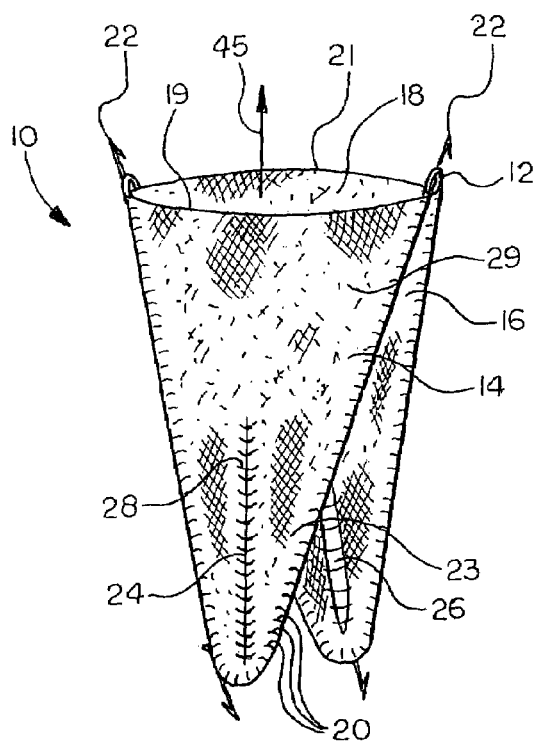
FIG. 3 is a perspective view of the medical device illustrated in FIG. 1 showing the device in an open configuration.
Figure 5:
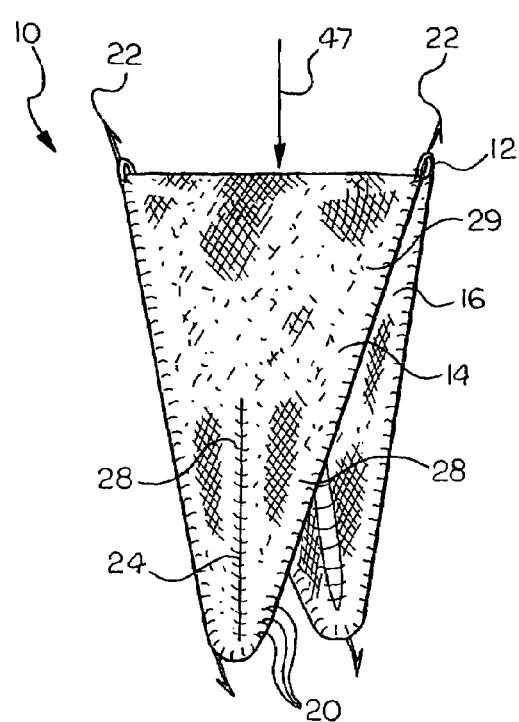
FIG. 5 is a perspective view of the medical device illustrated in FIG. 1 showing the device in a closed configuration.
Figure 8:
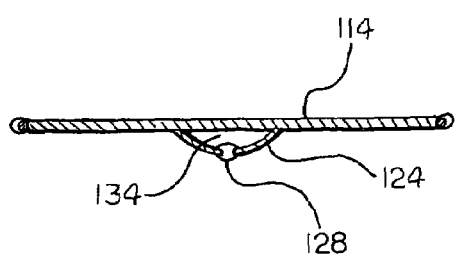
FIG. 8 is a sectional view of the medical device illustrated in FIG. 7 taken along line 8—8.

As best illustrated in FIGS. 1, 3, and 5, the medical device 10 of the first embodiment, includes a constraining portion 23 that comprises a gathered portion 24 of the material of the graft members 14, 16. The gathered portion 24 comprises two non-contiguous regions of an individual graft member 14, 16 that are drawn together to exclude an intervening portion 26. The non-contiguous regions are held together by any suitable connecting mechanism, such as sutures 28. In the finished medical device 10, the non-contiguous regions are disposed adjacent one another and maintained in that spatial relationship by the connecting mechanism, such as the sutures 28 illustrated in FIGS. 1, 3, and 5. The non-contiguous regions can be in contact with each other, along the entire length of the gathered portion 24 or a portion thereof. As best illustrated in FIG. 8, which illustrates an alternative embodiment described in detail below, contact between the non-contiguous regions of the gathered portion is not required.

Figure 4:
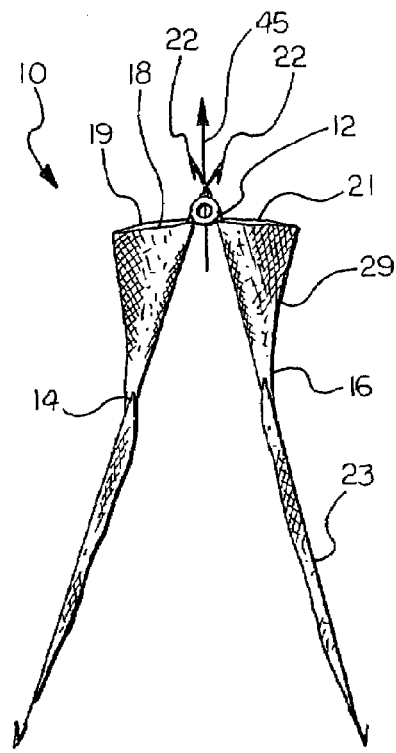
FIG. 4 is a side view of the medical device illustrated in FIG. 3.
Figure 6:
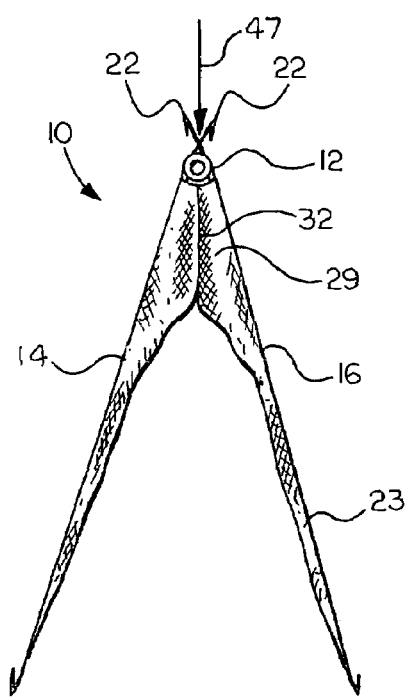
FIG. 6 is a side view of the medical device illustrated in FIG. 5.

The valve portion 29 is adapted to permit fluid flow through the body vessel in a first direction, represented by arrow 45 in FIGS. 3 and 4, and substantially prevent fluid flow through the body vessel in a second, opposite direction, represented by arrow 47 in FIGS. 5 and 6. The valve portion 29 can move between first and second positions to open and close the opening 18 and alternately permit and substantially prevent fluid flow through the opening.

As best illustrated in FIG. 1, the valve portion 29 can include pleats 30. As used herein, the term "pleat" refers to a fold, crease, bend or other transition in the material of a graft member. The term does not specifically require a permanent or semi-permanent crease in the material. As best illustrated in FIGS. 3 and 4, the valve portion 29 opens to enlarge opening 18 to permit fluid flow through the opening 18, and through the body vessel in which the device 10 is implanted, in a first direction 45. As best illustrated in FIGS. 5 and 6, the valve portion 29 closes opening 18 (not referenced in FIGS. 5 and 6, but contrast FIGS. 3 and 4) to substantially prevent fluid flow through the opening 18, and through the body vessel in which the device 10 is implanted, in a second, opposite direction 47. In this embodiment, the pleats 30 provide extra material in the valve portion 29 to ensure closure of the opening 18 when the valve portion 29 moves to a closed position.

The valve portion 29 can move between the open and closed configurations in response to a change in direction of fluid flow, such as a change from flow in the first direction 45 to a change of flow in the second, opposite direction 47. Also, the valve portion can move between open and closed configurations in response to a change in fluid pressure on one or more sides of the graft members 14, 16.

As illustrated in FIG. 6, the valve portions 29 can include sufficient material to form a coaptation region 32 between the graft members 14, 16. The coaptation region 32 is a length along which the graft members 14, 16 contact each other when the valve portions 29 of the graft members 14, 16 are in a closed configuration.

Figure 7:
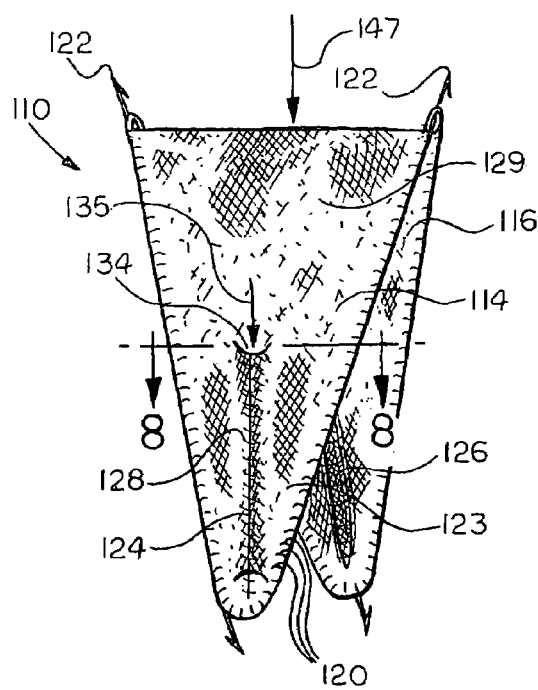
FIG. 7 is a perspective view of a medical device according to a second exemplary embodiment of the invention.

FIGS. 7 and 8 illustrate a medical device 110 according to a second exemplary embodiment of the invention. The device 110 illustrated in FIGS. 7 and 8 is similar to the device 10 illustrated in FIGS. 1 through 6, except as detailed below. Thus, the device 110 of this embodiment includes a support structure 112, graft members 114, 116, sutures 120, barbs 122, constraining portion 123, gathered portion 124, intervening portion 126, sutures 128, and valve portion 129. FIG. 7 illustrates the device 110 having the valve portion 129 in a closed configuration to substantially prevent fluid flow in the second opposite direction 147. The valve portion 129 operates in a manner similar to the valve portion 29 of the device 10 illustrated in FIGS. 1 through 6.

The medical device 110 includes passageway 134 in graft member 114 that allows a controlled amount 135 of fluid flow in the second, opposite direction to flow through the vessel in which the device 110 is implanted. The controlled amount 135 of flow is a portion of fluid flow 147. The passageway 134 defines a path extending from one portion, such as valve portion 129 or an upper part of constraining portion 123, of the device 110 to a second portion, such as a lower portion of the constraining portion 123, of the device 110. In the embodiment illustrated in FIG. 7, the gathered portion 124 defines the passageway 134.

The passageway 134 can have any suitable configuration, cross-sectional area, and length. The overall configuration, cross-sectional area, and length selected for the passageway 134 will depend on several factors, including the size and configuration of device 110, the size and configuration of the vessel in which the device 110 will be implanted, the extent of contact between the device 110 and the walls of the vessel, and the amount of retrograde flow through the vessel that is desired.

Figure 9:
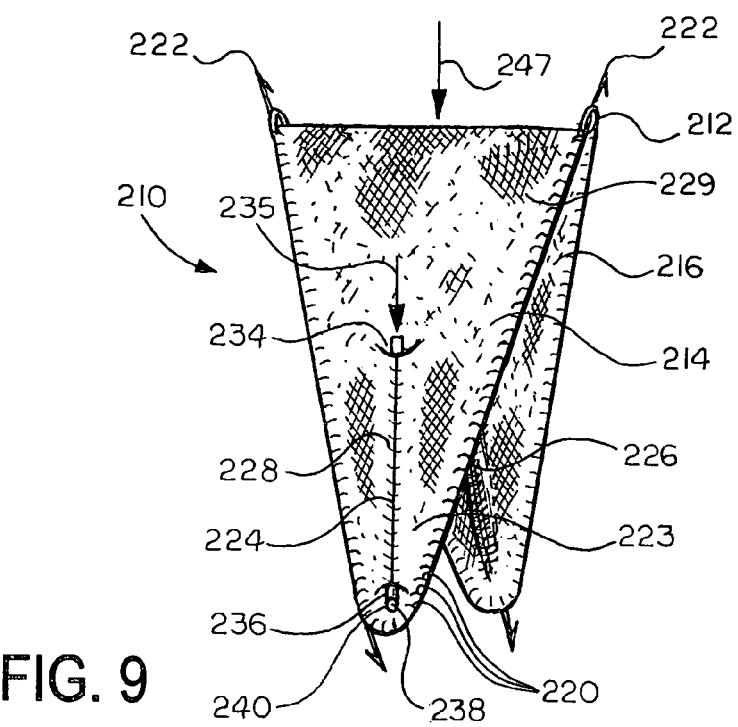
FIG. 9 is a perspective view of a medical device according to a third exemplary embodiment of the invention.

FIG. 9 illustrates a medical device 210 according to a third exemplary embodiment of the invention. The device 210 illustrated in FIG. 9 is similar to the device 110 illustrated in FIGS. 7 and 8, except as detailed below. Thus, the device 210 of this embodiment includes a support structure 212, graft members 214, 216, sutures 220, barbs 222, constraining portion 223, gathered portion 224, intervening portion 226, sutures 228, and valve portion 229. Also, the device 210 includes passageway 234. FIG. 9 illustrates the device 210 having the valve portion 229 in a closed configuration to substantially prevent fluid flow in the second opposite direction 247. The valve portion 229 operates in a manner similar to the valve portion 29 of the device 10 illustrated in FIGS. 1 through 6.

The medical device 210 includes a conduit 236 disposed in passageway 234. Conduit 236 can provide reinforcement to passageway 234, and may provide an interior surface of a material different than that of passageway 234. Conduit 236 can be formed of any suitable material, such as naturally occurring or synthetic materials, including polymeric tubing. The size and configuration of conduit 236 will largely depend on the size and configuration of passageway 234. Conduit 236 should be sized such that it can be retained in passageway 234 under physiological loads, either by friction fit, a suitable attachment mechanism, such as sutures, or any other suitable mechanism. Also, conduit 236 can be longer, shorter, or have the same length as passageway 234.

As illustrated in FIG. 9, conduit 236 includes an opening 238 that permits the exit of the controlled amount 235 of fluid flow from the passageway 234. Opening 238 can be defined by a beveled edge 240 on conduit 236. Beveled edge 240 can define a taper toward or away from the wall surface of the vessel in which the medical device 210 will be implanted.

Figure 10:
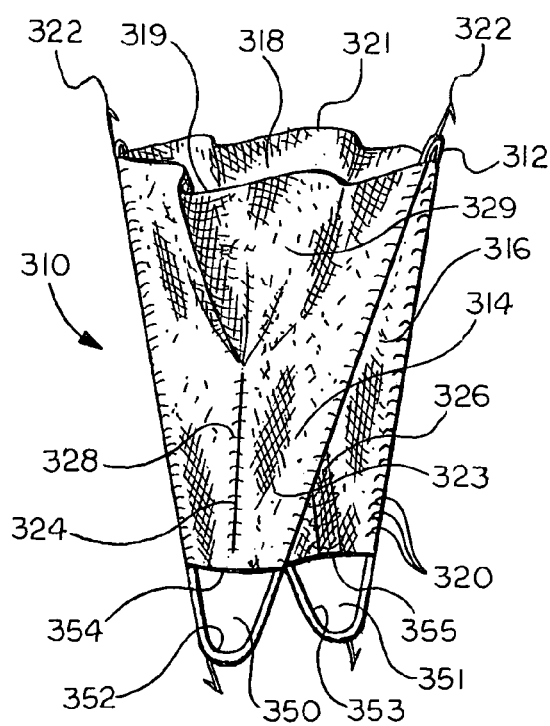
FIG. 10 is a perspective view of a medical device according to a fourth exemplary embodiment of the invention.

FIG. 10 illustrates a medical device 310 according to a fourth exemplary embodiment of the invention. The device 310 illustrated in FIG. 10 is similar to the device 10 illustrated in FIGS. 1 through 6, except as detailed below. Thus, the device 310 of this embodiment includes a support structure 312, graft members 314, 316, sutures 320, barbs 322, constraining portion 323, gathered portion 324, intervening portion 326, sutures 328, and valve portion 329. Free edges 319, 321 of the graft members 314, 316 cooperatively define an opening 318, and the valve portion 329 includes pleats 330. The valve portion 329 operates in a manner similar to the valve portion 29 of the device 10 illustrated in FIGS. 1 through 6.

Medical device 310 includes at least one opening 350 that permits a controlled amount of fluid flow in the second, opposite direction to flow through the vessel in which the device 310 is implanted. In this embodiment, the opening 350 is defined by an edge 354 of the graft member 314 and a portion 352 of the support structure 312. Opening 354 could also comprise a slit or other aperture in the graft member 314.

As illustrated in FIG. 10, the device can include first 350 and second 351 openings that permit a controlled amount of fluid flow in the second, opposite direction. If present, second opening 351 can be defined in a manner similar to that of opening 350, i.e., by an edge 355 of the graft member 316 and a portion 353 of the support structure 312, or in any other suitable manner, such as those described and illustrated herein.

Figure 11:
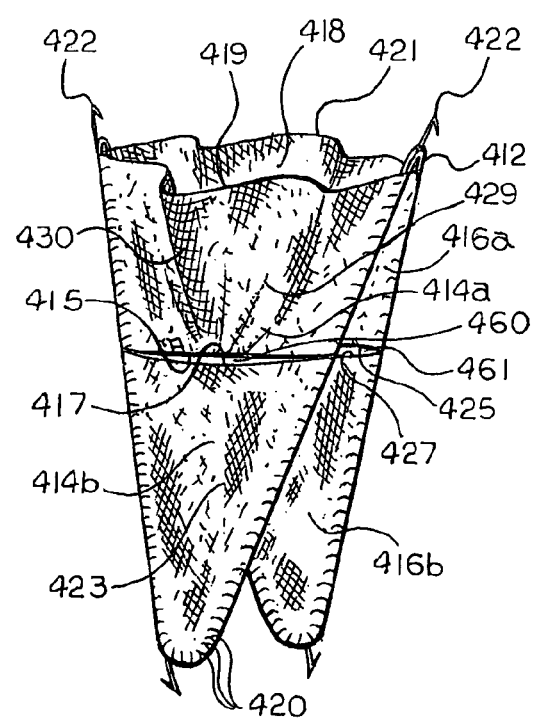
FIG. 11 is a perspective view of a medical device according to a fifth exemplary embodiment of the invention.

FIG. 11 illustrates a medical device 410 according to a fifth exemplary embodiment of the invention. The device 410 illustrated in FIG. 11 is similar to the device 10 illustrated in FIGS. 1 through 6, except as detailed below. Thus, the device 410 of this embodiment includes a support structure 412, graft members, sutures 420, barbs 422, constraining portion 423, and valve portion 429. Free edges 419, 421 of the graft members 414a, 416a cooperatively define opening 418, and the valve portion 429 includes pleats 430. The valve portion 429 operates in a manner similar to the valve portion 29 of the device 10 illustrated in FIGS. 1 through 6.

Medical device 410 includes an opening 460 defined by free edges 415, 417 of first 414a and second 414b graft members, respectively. Opening 460 permits a controlled amount of fluid flow in the second, opposite direction to flow through the vessel in which the device 410 is implanted. The first graft member 414a can form the valve portion 429, and the second graft member 414b can form the constraining portion 423. Opening 460 can also comprise a slit or other aperture in a single graft member.

As illustrated in FIG. 11, device 410 can include first 460 and second 461 openings that permit a controlled amount of fluid flow in the second, opposite direction. If present, the second opening 461 can be defined in a manner similar to that of opening 460, i.e., by edges 425 and 427 of third 416a and fourth 416b graft members, or in any other suitable manner, such as those described and illustrated herein.

In this embodiment, the graft members 414a, 414b, 416a, 416b can be formed of the same or different materials. The use of different materials may be advantageous at least because it provides a degree of control to the constrained expansion. For example, two materials having different compliance properties could be used. In one exemplary embodiment, the first graft member 414a is formed of a material that is more compliant than the material from which the second graft member 414b is formed. This configuration allows the second graft member 414b to constrain the expansion of the support structure 412, thereby providing the constraining portion 423, and allows the first graft member 414a to provide the valve portion 429.

If two different materials are desired, any suitable pairing of materials can be used. The materials chosen need only have the desired difference in compliance properties or in any other desired property.

An example of a suitable pairing of materials is a natural material and a synthetic material. In one exemplary embodiment, a polymer, such as polypropylene, is used to form one graft member and an extracellular matrix material, such as submucosa, is used to form another graft member. Furthermore, the graft members 414a, 414b can be formed of the same material, but can be treated, or processed, or made in different manners that produce the desired different properties. For example, one graft member can be formed from a extracellular matrix material and another graft member can be formed of an extracellular matrix material that has been fixed, such as by chemical processing.

In embodiments in which two materials are used, the materials can be disposed on the support structure in a manner that forms an opening, such as the opening 460 illustrated in FIG. 11, or the materials can be attached to each other in any suitable manner to partially or completely eliminate any opening between the graft members. For example, the two graft members can be joined by an attachment element, such as a suture, an adhesive, or a clip. Also, the graft members can be joined together, such as by tissue welding, melt forming, or any other suitable process.

In the embodiments that include openings that permit a controlled amount of fluid flow in the second, opposite direction to flow through the vessel in which the device is implanted, the dimensions, configuration, and number of the openings can be optimized based upon the vessel in which the device is implanted. The size and configuration selected will depend on several factors, including the vessel size, typical flow volumes and rates, and others. The opening should be sized to allow a desired amount of retrograde flow to occur, while remaining sufficiently small to still allow the medical device to act as a valve. Thus, the opening can be sized so as to not allow a majority of retrograde flow to pass through the opening. The total open area of the opening should be less than the cross-sectional area of the vessel lumen.

The opening can be sized to mimic the degree of retrograde flow—the leakiness—that is present in a natural valve located at the point of treatment. In these embodiments, the dimensions of the opening can be determined and optimized based upon the vessel in which the device is to be placed. The total open area of the opening can be less than about 50% of the cross-sectional area of the vessel, or less than about 25% of the total cross-sectional area of the vessel. In one particular example, a device is configured for placement in a vessel having a total cross-sectional area of about 50 mm$^2$. In this example, the opening has a total open area of about 20 mm$^2$.

In devices including multiple openings that permit a controlled amount of fluid flow in the second, opposite direction to flow through the vessel in which the device is implanted, the total open area of all openings can be optimized as described above, but it is not necessary that the individual openings have equivalent total open areas.

Figure 12:
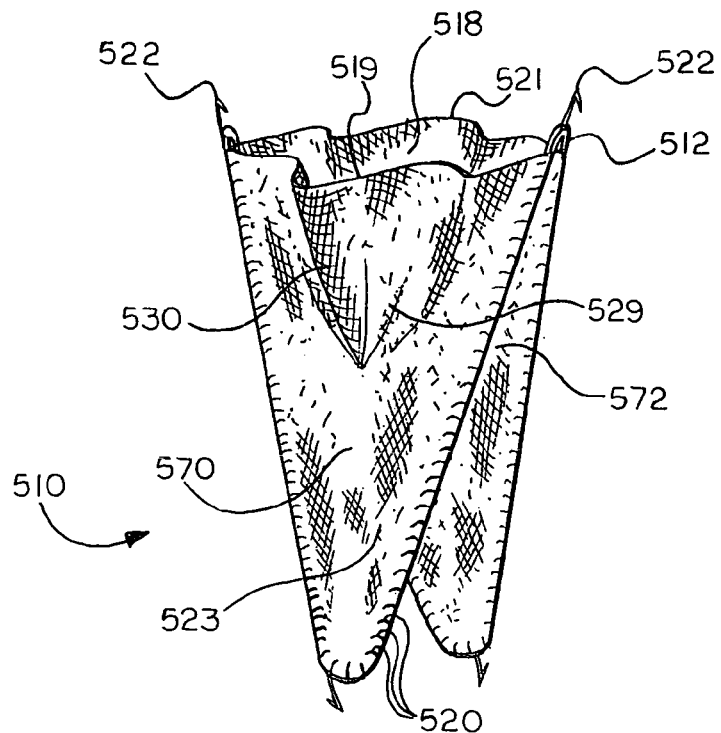
FIG. 12 is a perspective view of a medical device according to a sixth exemplary embodiment of the invention.
Figures 13, 14:
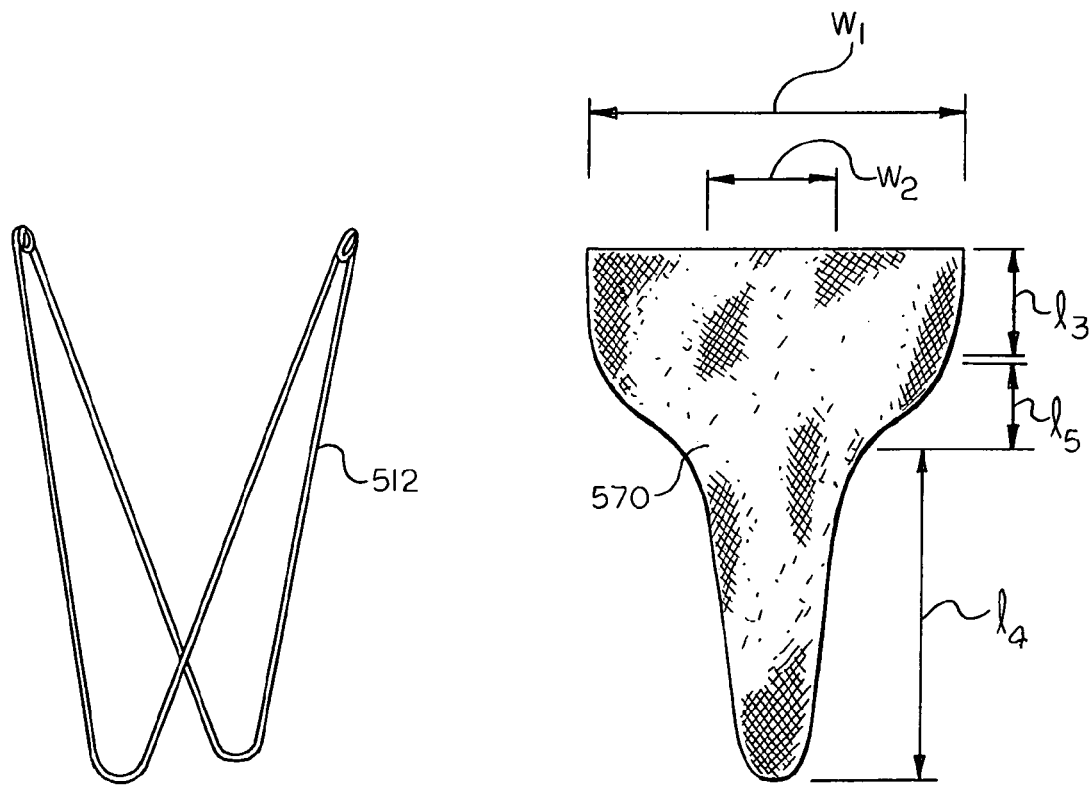
FIG. 13 is a perspective view of the support structure of the medical device illustrated in FIG. 12.
FIG. 14 is a side view of the graft member of the medical device illustrated in FIG. 11.

FIG. 12 illustrates a medical device 510 according to a sixth exemplary embodiment of the invention. The device 510 illustrated in FIG. 12 is similar to the device 10 illustrated in FIGS. 1 through 6, except as detailed below. Thus, the device 510 of this embodiment includes a support structure 512, sutures 520, barbs 522, constraining portion 523, and valve portion 529. Free edges 519, 521 of the graft members 570, 572 cooperatively define opening 518, and the valve portion 529 includes pleats 530. The valve portion 529 operates in a manner similar to the valve portion 29 of the device 10 illustrated in FIGS. 1 through 6. FIG. 13 illustrates the support structure 512 of the device 510 illustrated in FIG. 12, without the attached graft members 570, 572. FIG. 14 illustrates one graft member 570 prior to attachment to the support structure 512.

In this embodiment, graft members 570, 572 are configured to have at least two distinct portions $l_3$ and $l_4$ that individually correspond to the valve 529 and constraining portions 523. The portions $l_3$, $l_4$ differ from each other in at least one dimension. For example, FIG. 14 illustrates portion $l_3$ as having a width $w_1$ that is greater than a width $w_2$ of portion $l_4$. When graft member 570 is attached to support structure 512, support structure 512 is constrained by the smaller width $w_2$ of portion $l_4$, while support structure 512 is not constrained, or is constrained to a lesser degree, by the larger width $w_1$ of portion $l_3$. Thus, in device 510, portion $l_4$ is drawn taught, providing constraining portion 523, while portion $l_3$ is not taught, providing pleats 530 and valve portion 529. This configuration of graft members 570, 572 may eliminate the need for a gathered portion, such as gathered portion 24 of the device 10 illustrated in FIGS. 1 through 6.

As illustrated in FIG. 14, graft member 570 may include transition portion $l_5$ that defines a taper between the larger width $w_1$ of portion $l_3$ and the smaller width $w_2$ of portion $l_4$.

Figure 15:
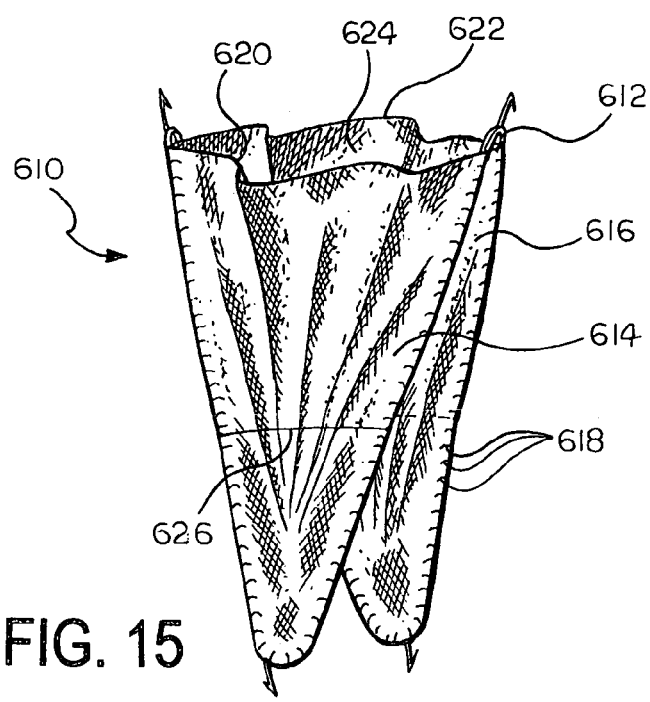
FIG. 15 is a perspective view of a medical device according to a seventh exemplary embodiment of the invention.

FIG. 15 illustrates a medical device 610 according to a seventh exemplary embodiment of the invention. The device 610 of this embodiment includes a support structure 612 and first 614 and second 616 graft members. Each graft member 614, 616 is attached to the support structure 612 by attachment elements, such as sutures 618. Free edges 620, 622 of graft members 614, 616, respectively, cooperatively define an opening 624. Together, the graft members 614, 616 permit fluid flow through a body vessel in which the device 610 is implanted in a first direction and substantially prevent fluid flow through the body vessel in a second, opposite direction. The graft members 614, 616 accomplish this by opening and closing the opening 624 in response to changes in pressure, fluid flow direction, or other parameters.

In this embodiment, the support structure is prevented from achieving its second, expanded configuration by a constraining member 626 that is attached to the support structure 612 and is distinct from the graft members 614, 616. In the embodiment illustrated in FIG. 15, the constraining member 626 comprises a suture tied to opposite portions of the support structure and disposed across a graft member 614. The constraining member 626 can be disposed at any suitable positions on the support structure 612, such as at or below a midpoint relative to the opening 624 and the opposing end of the support structure 612.

Figure 16:
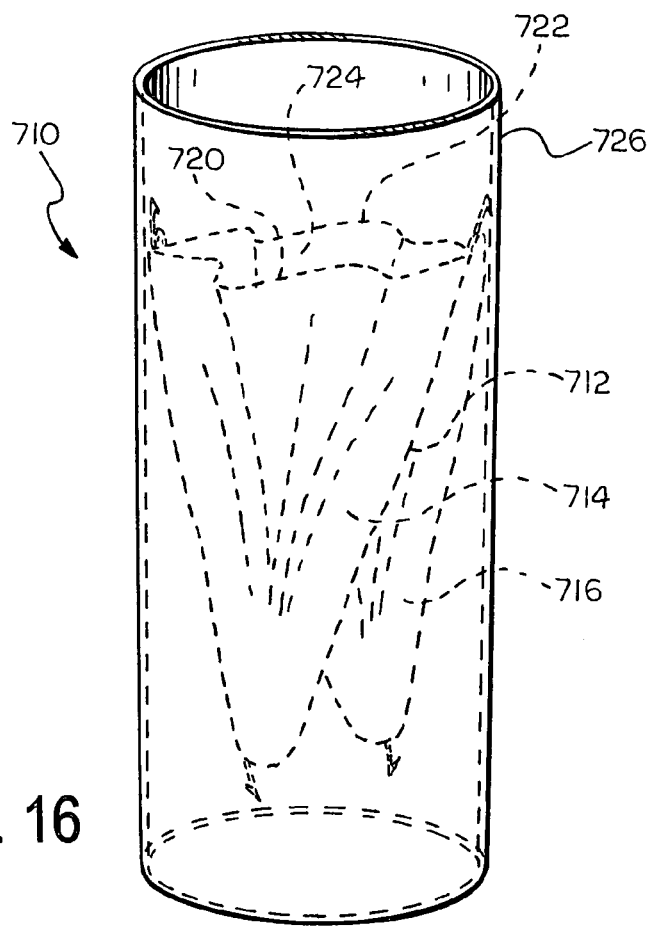
FIG. 16 is a perspective view of a medical device according to an eighth exemplary embodiment of the invention.

FIG. 16 illustrates a medical device 710 according to an eighth exemplary embodiment of the invention. The device 710 of this embodiment is similar to the device 610 illustrated in FIG. 15, except as described below. Thus, the device 710 includes a support structure 712, and first 714 and second 716 graft members attached to the support structure 712 by attachment elements, such as sutures (not illustrated in FIG. 16). Free edges 720, 722 of graft members 714, 716, respectively, cooperatively define an opening 724. Together, the graft members 714, 716 permit fluid flow through a body vessel in which the device 710 is implanted in a first direction and substantially prevent fluid flow through the body vessel in a second, opposite direction. The graft members 714, 716 accomplish this by opening and closing the opening 724 in response to changes in pressure, fluid flow direction, or other parameters.

In this embodiment, the support structure 712 is prevented from achieving its second, expanded configuration by a constraining member 726 disposed about the support structure 712 and is distinct from the graft members 714, 716.

In the illustrated embodiment, the constraining member 726 comprises a sleeve disposed circumferentially about the support structure 712. The constraining member 726 can be attached to the support structure 712 or other portion of the medical device, such as graft members 712, 714, by any suitable attachment element, such as adhesives, sutures, and thermal bonding. Alternatively, the constraining member 726 can be secured to the support structure 712 through an interference fit that arises due to the constraining nature of the constraining member 726.

In all embodiments, the support structure of the medical device can be constrained to any suitable degree relative to its second, expanded configuration. It is expected to be advantageous to constrain the support structure to a degree that allows the medical device to achieve a diameter from implantation that is larger than the resting diameter of the body vessel in which the device is implanted but that is smaller than a diameter at which an adverse effect can occur, such as rupture of the body vessel. For example, a prosthetic venous valve according to one exemplary embodiment of the invention is designed for implantation in a vein. It is expected that the prosthetic valve will be advantageous if the support structure is constrained from expanding beyond about 1.5 times the resting diameter of the body vessel at a desired point of implantation. It is expected to be particularly advantageous for the support structure to be constrained from expanding beyond about 1.2 times the resting diameter of the body vessel at a desired point of implantation.

The invention also provides methods of making medical devices for implantation in a body vessel. FIG. 17 illustrates a flow chart of a method 800 according to one embodiment of the invention. The method comprises a step 802 of providing a support structure, a step 804 of providing a graft member, a step 806 of attaching the graft member to the support structure, a step 808 of forming a valve portion, and a step 810 of constraining the support structure. In the constraining step 810 of one exemplary method according to the invention, a graft member is manipulated so that a portion of the graft member constrains the expansion of the support structure but the valve portion does not constrain the support structure, or does so to a lesser degree than another portion of the graft member. The step 808 of forming a valve portion and the step 810 of constraining the support structure can be accomplished in one step that achieves both functions. For example, the support structure and graft member can be disposed, together, on a mandrel with structural features that are complementary to the valve and constraining portions of the medical device. The mandrel can define a recess that allows slack in an area that will become the valve portion, and can define a structural feature that draws the graft member taught in an area that will become the constraining portion. The material can be placed on such a mandrel, and the support structure can then be disposed on the material. While the assembly is still on the mandrel, the graft member can be attached to the support structure. With some materials, such as extracellular matrix materials, it may be advantageous to keep the materials wet during some or all manufacturing steps. This is expected to provide a desired degree of control over the formation of the valve and/or constraining portions.

The invention also provides methods of treating a patient. FIG. 18 illustrates a flow chart of a method according to one embodiment of the invention. The method 900 comprises a step 902 of providing a medical device according to the invention, a step 904 of delivering the medical device to a point of treatment in a body vessel, and a step 906 of deploying the medical device at the point of treatment. The delivering step 904 can comprise delivery by surgical or by percutaneous delivery techniques known to those skilled in the art.

The foregoing description of exemplary embodiments of the invention includes the best mode for practicing the invention. It is intended to aid in the understanding of the invention, and not to limit the invention or its protection in any manner.

We claim:

1. A medical device for implantation in a body vessel, comprising:
   a support structure having a first, unexpanded configuration and a second, expanded configuration; and
   a graft member connected to the support structure and comprising a valve portion and a constraining portion, the valve portion adapted to permit fluid flow through said vessel in a first direction and substantially prevent fluid flow through said vessel in a second, opposite direction, and the constraining portion comprising a gathered portion of the graft member that includes first and second non-contiguous regions of the graft member held adjacent one another by a connecting mechanism, the constraining portion adapted to substantially prevent the support structure from achieving the second, expanded configuration.

2. The medical device of claim 1, wherein the gathered portion defines a passageway adapted to permit a controlled amount of fluid flow through said body vessel in the second, opposite direction.

3. The medical device of claim 1, wherein the graft member comprises an extracellular matrix material.

4. The medical device of claim 1, wherein the graft member comprises small intestine submucosa.

5. The medical device of claim 1, wherein the graft member defines an edge substantially free of the support structure, the edge cooperating with a portion of the support structure to define an opening adapted to permit a controlled amount of fluid flow through said body vessel in the second, opposite direction.

6. The medical device of claim 5, wherein the edge is defined by the constraining portion of the graft member.

7. A medical device for implantation in a body vessel, comprising:
   a support structure having a first, unexpanded configuration and a second, expanded configuration; and
   a graft member connected to the support structure and comprising a valve portion and a constraining portion, the valve portion adapted to permit fluid flow through said vessel in a first direction and substantially prevent fluid flow through said vessel in a second, opposite direction, and the constraining portion comprising a gathered portion of the graft member and adapted to substantially prevent the support structure from achieving the second, expanded configuration;
   wherein the gathered portion defines a passageway adapted to permit a controlled amount of fluid flow through said body vessel in the second, opposite direction; and
   further comprising a cannula disposed in the passageway.

8. The medical device of claim 7, wherein the cannula comprises a distal end disposed near the valve portion of the graft member and a proximal end disposed near the constraining portion of the graft member, and wherein the proximal end defines an opening angulated with respect to the graft member.

9. A medical device for implantation in a body vessel, comprising:
   a support structure; and
   first and second graft members connected to the support structure, each of the graft members comprising a valve portion and a constraining portion, the valve portions being disposed substantially opposite one another and adapted to cooperatively permit fluid flow through said vessel in a first direction and substantially prevent fluid flow through said vessel in a second, opposite direction;
   wherein at least one of the constraining portions comprises a gathered portion of one of the first and second graft members, the gathered portion including first and second non-contiguous regions of the graft member held adjacent one another by a connecting mechanism;
   wherein the constraining portions cooperate to substantially prevent the support structure from achieving the second, expanded configuration.

10. The medical device of claim 9, wherein the gathered portion defines a passageway adapted to permit a controlled amount of fluid flow through said body vessel in the second, opposite direction.

11. The medical device of claim 9, wherein the graft member comprises an extracellular matrix material.

12. The medical device of claim 9, wherein the graft member comprises small intestine submucosa.

13. A medical device for implantation in a body vessel, comprising:
   a support structure; and
   first and second graft members connected to the support structure, each of the graft members comprising a valve portion and a constraining portion, the valve portions being disposed substantially opposite one another and adapted to cooperatively permit fluid flow through said vessel in a first direction and substantially prevent fluid flow through said vessel in a second, opposite direction;
   wherein at least one of the constraining portions comprises a gathered portion of one of the first and second graft members;
   wherein the constraining portions cooperate to substantially prevent the support structure from achieving the second, expanded configuration;
   wherein the gathered portion defines a passageway adapted to permit a controlled amount of fluid flow through said body vessel in the second, opposite direction; and
   further comprising a cannula disposed in the passageway.

14. The medical device of claim 13, wherein the cannula comprises a distal end disposed near the valve portion of the graft member and a proximal end disposed near the constraining portion of the graft member, and wherein the proximal end defines an opening angulated with respect to the graft member.

15. A prosthetic valve for implantation in a body vessel, comprising:
   a support structure having a first, unexpanded configuration and a second, expanded configuration;
   a first valve leaflet connected to the support structure and comprising a first valve portion and a first constraining portion comprising a gathered portion of the first valve leaflet that includes first and second non-contiguous regions of the first valve leaflet held adjacent one another by a first connecting mechanism; and
   a second valve leaflet connected to the support structure and comprising a second valve portion and a second constraining portion comprising a gathered portion of the second valve leaflet that includes third and fourth non-contiguous regions of the second valve leaflet held adjacent one another by a second connecting mechanism;
   wherein the first and second valve portions cooperatively regulate fluid flow through said body vessel; and
   wherein the first and second constraining portions cooperatively prevent the support structure from achieving the second, expanded configuration.

* * * * *